US012672865B2

(12) United States Patent
Alfonso et al.

(10) Patent No.: US 12,672,865 B2
(45) Date of Patent: Jul. 7, 2026

(54) BACKSTOP LOADER

(71) Applicant: Conmed Corporation, Utica, NY (US)

(72) Inventors: Gregory Alfonso, Seffner, FL (US); Matthew Summitt, Palm Harbor, FL (US); Robert Thibodeau, Saint Petersburg, FL (US)

(73) Assignee: Conmed Corporation, Utica, NY (US)

( * ) Notice: Subject to any disclaimer, the term of this patent is extended or adjusted under 35 U.S.C. 154(b) by 113 days.

(21) Appl. No.: 17/278,132

(22) PCT Filed: Sep. 24, 2019

(86) PCT No.: PCT/US2019/052571
§ 371 (c)(1),
(2) Date: Mar. 19, 2021

(87) PCT Pub. No.: WO2020/068732
PCT Pub. Date: Apr. 2, 2020

(65) Prior Publication Data
US 2021/0330315 A1 Oct. 28, 2021

Related U.S. Application Data

(60) Provisional application No. 62/735,284, filed on Sep. 24, 2018.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0404* (2013.01);
(Continued)

(58) Field of Classification Search
CPC ............ A61B 17/0401; A61B 17/0409; A61B 2017/0414; A61B 2017/0404;
(Continued)

(56) References Cited

U.S. PATENT DOCUMENTS

| | | | |
|---|---|---|---|
| 6,511,498 B1 | 1/2003 | Fumex | |
| 8,795,295 B2 * | 8/2014 | Sauer ................. | A61B 17/0401 606/139 |

(Continued)

FOREIGN PATENT DOCUMENTS

JP 2015-533302 A2 11/2015

OTHER PUBLICATIONS

JP Office Action, App. No. 2021516409, dated Jun. 14, 2022, pp. 1-12.
(Continued)

*Primary Examiner* — Kathleen S Holwerda
*Assistant Examiner* — James R McGinnity
(74) *Attorney, Agent, or Firm* — Bond, Schoeneck & King, PLLC; Frederick J.M. Price

(57) ABSTRACT
A suture backstop system including a backstop with a first and second end both extending in a distal direction. The system includes a first passing longitudinal element woven through the backstop. A first loop is created in the first passing longitudinal element and extends from the first end of the backstop. Similarly, the system also includes a second passing longitudinal element woven through the backstop where a second loop is created in the second passing longitudinal element and extends from the second end of the backstop. The first and second passing longitudinal elements are attached to a distal end of a handle. The first and second ends of the backstop are positioned in a first direction in an undeployed configuration and positioned in a second direction, different from the first direction, in a deployed configuration.

9 Claims, 9 Drawing Sheets

(52) U.S. Cl.
CPC ................. *A61B 2017/0409* (2013.01); *A61B 2017/0414* (2013.01); *A61B 2017/0446* (2013.01); *A61B 2017/0464* (2013.01); *A61F 2002/0852* (2013.01); *A61F 2002/0882* (2013.01)

(58) Field of Classification Search
CPC .... A61B 2017/0446; A61B 2017/0464; A61B 2017/0406; A61F 2/0811; A61F 2/0852; A61F 2002/0882; A61F 2/08
See application file for complete search history.

(56) References Cited

U.S. PATENT DOCUMENTS

| | | | | |
|---|---|---|---|---|
| 8,986,327 | B2 * | 3/2015 | Karasic | .............. A61B 17/1633 606/144 |
| 2012/0283749 | A1 | 11/2012 | Sauer | |
| 2012/0290004 | A1 * | 11/2012 | Lombardo | ......... A61B 17/0401 606/232 |
| 2013/0110165 | A1 * | 5/2013 | Burkhart | ........... A61B 17/0401 606/232 |
| 2018/0008258 | A1 * | 1/2018 | Phisitkul | .......... A61B 17/06166 |

OTHER PUBLICATIONS

KR Office Action, App. No. 10-2021-700823, dated Dec. 27, 2022, pp. 3-12.
International Search Report Form PCT/ISA/220, International Application No. PCT/US2019/052571, pp. 1-11, Dated Dec. 13, 2019.
Translated Chinese First Office Action, App. No. 201980062861.3, dated Nov. 28, 2023, pp. 1-14.

* cited by examiner

BACKSTOP LOADER

CROSS-REFERENCES TO RELATED APPLICATIONS

This application is a national stage application under 35 U.S.C. 371 based on international patent application PCT/US19/52571 filed on Sep. 24, 2019, which claims priority to U.S. Provisional Patent Application Ser. No. 62/735,284 filed on Sep. 24, 2018 and entitled "Backstop Loader," the entireties of which are incorporated herein by reference.

BACKGROUND OF THE INVENTION

1. Field of the Invention

The present invention is directed generally to surgical devices for repair and reconstruction of soft tissue injuries and, more particularly, to a suture backstop system for loading an all-suture backstop on a suspension system in a bone tunnel.

2. Description of Related Art

Many common surgical procedures involve the repair and reconstruction of torn or damaged soft tissue. For example, in common arthroscopic surgical procedures, a replacement graft ligament is secured at the site of the original, now damaged, ligament. The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing a graft ligament within these bone tunnels. In many applications, such as in the knee joint, such procedures may be performed arthroscopically. The graft ligament may be an autograft, an allograft, a xenograft, or it may be totally artificial and synthetic. Common types of anterior cruciate ligament (ACL) grafts, for example, include ones which may be autologous or allograft bone-patellar tendon-bone or soft tissue (such as semitendinosus and gracilis tendons), both types harvested by techniques well known to those skilled in the art.

The graft ligaments may be secured within the bone tunnels in a variety of ways. Of prime importance is the degree to which they can withstand pullout forces prior to complete healing. For example, it is known to use interference screws inserted parallel to the tunnel axis to compress the ends of the graft ligament against the wall of the bone tunnel to secure the graft ligament and promote tissue in-growth.

Suspensory graft fixation devices have been developed to secure a graft ligament in a bone tunnel. One such device is described in U.S. Pat. No. 8,852,250 (Lombardo et al.), entitled Graft Fixation Implant, assigned to the assignee hereof and incorporated by reference in its entirety herein. Suspensory graft fixation devices work by lying transversely across the opening of a bone tunnel and generally take the form of an elongated anchor member which suspends a graft retaining loop from a fixation point on the surface of a bone to which the graft is to be attached (in this case, a femur). The elongated member has an axis and a pair of suture receiving apertures symmetrically situated on the axis on opposite sides of the center of the elongated member. In ACL procedures, the elongated member, often called a button, is adapted to be situated transversely across the exit opening of the bone tunnel on the lateral femoral cortex so that a supporting loop, generally made of suture material, can be suspended from the button and can extend into the bone tunnel from the suture receiving apertures of the button. The suture loop supports one end of a graft ligament passed through the loop.

The term "suture" as used herein may be any type of filamentous material such as a biocompatible or bioabsorbable filament, ribbon, tape, woven or non-woven material capable of providing the loop support and the frictional resistance required by the device described herein. In arthroscopic procedures, such as an ACL reconstruction, the elongated anchor member is initially aligned with the axis of the bone tunnel, and pulled through the tunnel to the exit at the distal end on the lateral femur. For such suspensory graft fixation devices to be able to support a graft ligament and to be properly transversely situated at the exit of the bone tunnel, the suture loop and the bone tunnel must both be long enough to enable the elongated member to "flip" from an axially aligned orientation to a transverse orientation when it exits the bone tunnel.

Since the supporting loop of such a suspensory device is most often of a fixed length, graft fixation requires preparation of a graft ligament of predetermined length. Furthermore, because conventional art suspensory graft fixation devices have fixed loop lengths, they are produced in multiple sizes (ranging, for example, from loop lengths of 15 mm to 60 mm in 5 mm increments in the case of XO Button® implants made by ConMed Corporation, Largo, Fla.) in order to accommodate various graft and tunnel lengths that may be encountered during a surgical procedure. The fixed graft length and variations in tunnel and loop lengths can make conventional suspensory ligament fixation challenging.

However, when using buttons (or other backstops), the surgeon loads the suture tails through the button and then ties down the construct. In order to use an all-suture construct, such as a suture braid, as a button, the user must pierce or weave the all-suture construct with the suture tails to create a button. This is a complicated process that can take numerous, time-consuming steps.

Therefore, there is a need for a suture backstop system that can load an all-suture button or other backstop onto sutures quickly and easily.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a suture backstop system for loading an all-suture backstop on a suspension system in a bone tunnel. According to one aspect, the suture backstop system has a backstop with a first end and a second end both extending in a distal direction.

The system includes a first passing longitudinal element (such as a wire (e.g., nitinol) or other element stiffer than suture, but could also be suture) woven through the backstop such that a first loop is created in the first passing longitudinal element and extends from the first end of the backstop. Similarly, the system can also include a second passing longitudinal element (similar to the first passing longitudinal element) woven through the backstop such that a second loop is created in the second passing longitudinal element and extends from the second end of the backstop. The first and second passing longitudinal elements can be attached to a distal end of a handle.

According to another aspect, the suture backstop system has a backstop having a first end and a second end. The first and second ends are positioned and extend in a first direction in an undeployed configuration and are positioned and extend in a second direction, different from the first direction, in a deployed configuration. The system includes a first passing longitudinal element woven through the backstop such that a first loop is created in the first passing longitudinal element and extends from the first end of the backstop. Similarly, the system also includes a second passing longitudinal element woven through the backstop such that a second loop is created in the second passing longitudinal element and extends from the second end of the backstop.

According to another aspect, the present invention is a method for suspending a first body in relative position to a second body. The method includes the steps of: (i) providing a suspension system comprising a length of suture with a pair of free limbs positioned through an anchoring body; (ii) passing the free limbs through a proximal first body and an adjacent distal second body such that the free limbs extend from a proximal surface of the first body and a portion of the anchoring body is positioned on a distal surface of the second body; (iii) providing a suture backstop system comprising a backstop having a first end and a second end both extending in a distal direction, a first passing longitudinal element woven through the backstop such that a first loop is created in the first passing longitudinal element and extends from the first end of the backstop, a second passing longitudinal element woven through the backstop such that a second loop is created in the second passing longitudinal element and extends from the second end of the backstop, and a handle having a distal end attached to the first passing longitudinal element and the second passing longitudinal element; (iv) passing the free limbs through the first and second loops; (v) pulling the free limbs in a distal direction and pulling the handle in a proximal direction, causing the first and second loops to pull the free limbs through the backstop; (vi) removing the handle from the backstop; (vii) positioning the backstop at a proximal surface of the first proximal body by pulling the free limbs, wherein pulling the free limbs deploys the backstop over the proximal surface of the first proximal body; (ix) tying a knot in the free limbs proximal to the backstop; and (x) cutting the free limbs at a position proximal to the knot.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
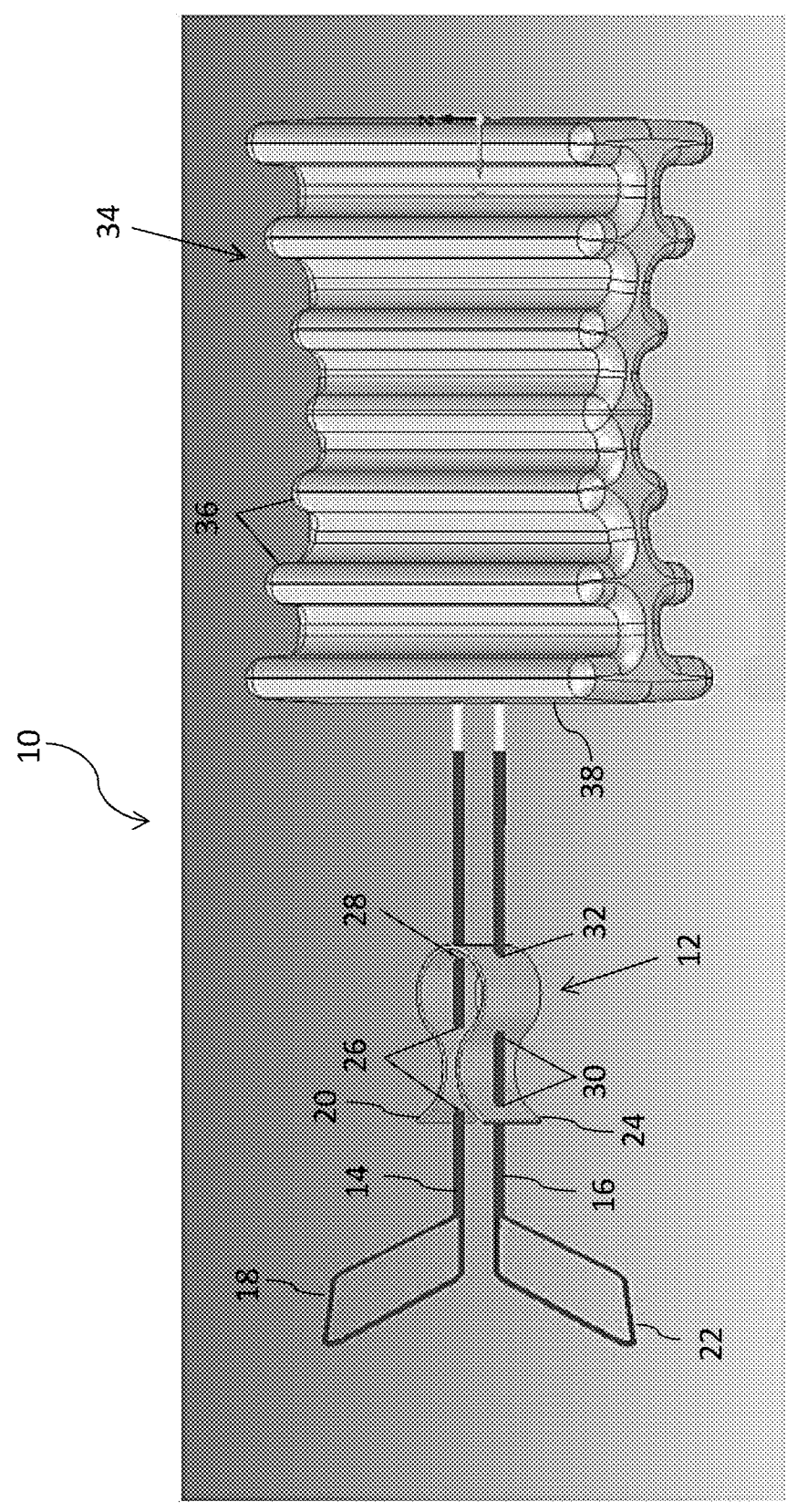
FIG. 1 is a top perspective view schematic representation of a suture backstop system, according to an embodiment.

Referring now to the figures, wherein like reference numerals refer to like parts throughout, FIG. 1 shows a top perspective view schematic representation of a suture backstop system 10, according to an embodiment. The suture backstop system 10 comprises a backstop 12 with a pair of passing longitudinal elements (as shown in this example, a first passing wire 14 and a second passing wire 16) woven therethrough. The backstop 12 may be a button, suspensory fixation device, or other anchor composed of any soft, flexible suture anchor material (similarly as discussed with respect to anchoring body 112—including described functionality—with respect to FIGS. 6-7 below). A purpose of using an all-suture anchor backstop 12 and an all-suture button 112 is to minimize irritation and discomfort to the patient at the surgical site. In the depicted embodiment, the backstop 12 can be composed of suture braid. In alternative embodiments, the backstop 12 can be composed of radiopaque fiber such that the backstop 12 can be seen in x-ray photographs. An all-suture backstop 12 minimizes irritation and discomfort to the patient at the surgical site. The passing wires 14, 16 can be composed of any suitable wire material, including but not limited to nitinol (which should be understood and appreciated by a person of ordinary skill in the art in conjunction with a review of this disclosure), as should be understood by a person of ordinary skill in the art in conjunction with a review of this disclosure, such as nitinol.

Still referring to FIG. 1, the passing wires 14, 16 are woven through the backstop 12 such that a first loop 18 is created in the first passing wire 14 and extends distally from a first end 20 of the backstop 12, and a second loop 22 is created in the second passing wire 16 and extends distally from a second end 24 of the backstop 12. In an embodiment, the first passing wire 14 is folded in half to create the first loop 18 and the limbs of the first passing wire 14 are woven through the backstop 12 in the proximal direction. Similarly, the second passing wire 16 is folded in half to create the second loop 22 and the limbs of the second passing wire 16 are woven through the backstop 12 in the proximal direction.

In the depicted embodiment, the passing wires 14, 16 pass through the backstop 12 a total of six (6) times (although, the number of pass throughs can vary, and can be an even number on one side and an odd number on another side of the backstop 12 (or both even or both odd)). Specifically, the first loop 18 extends distally from the first end 20 of the backstop 12 and the first passing wire 14 is woven proximally through the backstop 12 at three passing locations 26, 28. The first passing wire 14 is woven such that it extends from the backstop 12 at a first central passing location 28 (as used herein, "central" describes a location on the backstop 12 closer to a midpoint or center of the backstop 12 as compared to the first or second end 20, 24 of the backstop 12).

As with the first loop 18, the second loop 22 extends distally from the second end 24 of the backstop 12 and the second passing wire 16 is woven proximally through the backstop 12 at three passing locations 30, 32. The second passing wire 16 is woven such that it extends from the backstop 12 at a second central passing location 32, which is adjacent to the first central passing location 28, as shown in FIG. 1. Thus, in a pre-deployment configuration shown in FIG. 1, the backstop 12 is folded such that the first end 20 and the second end 24 are adjacent with the first loop 18 and the second loop 22 both extending in the distal direction, while the first and second passing wires 14, 16 extend in the proximal direction.

The suture backstop system 10 of FIG. 1 also includes a handle 34. In the depicted embodiment, the handle 34 is rectangular; however any other suitable geometry can be used. In addition, the handle 34 may be molded such that it comprises one or more ridges 36 (or other projections) for increased gripping control for the user. The first passing wire 14 extending from the first loop 18 and the second passing wire 16 extending from the second loop 22 are attached to a distal end 38 of the handle 34, as shown. With the suture backstop system 10 in the pre-deployment configuration, as shown in FIG. 1, the suture backstop system 10 can be used to load the backstop 12 onto a suspension system for suspending or tensioning a first body in a desired position relative to a second body.

Figure 5:
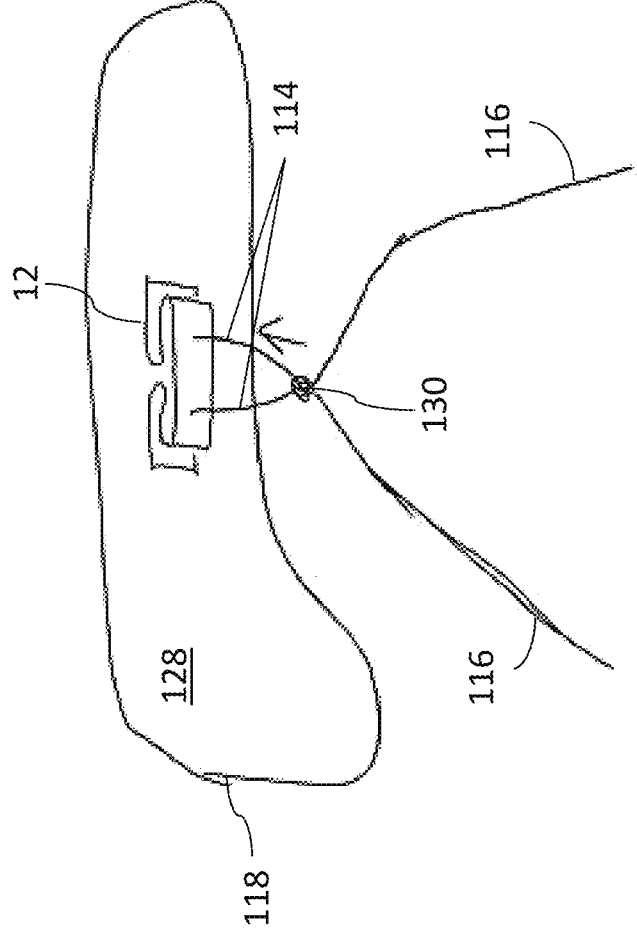
FIG. 5 is a side view schematic representation of the backstop in the deployed configuration, according to an embodiment.
Figure 6:
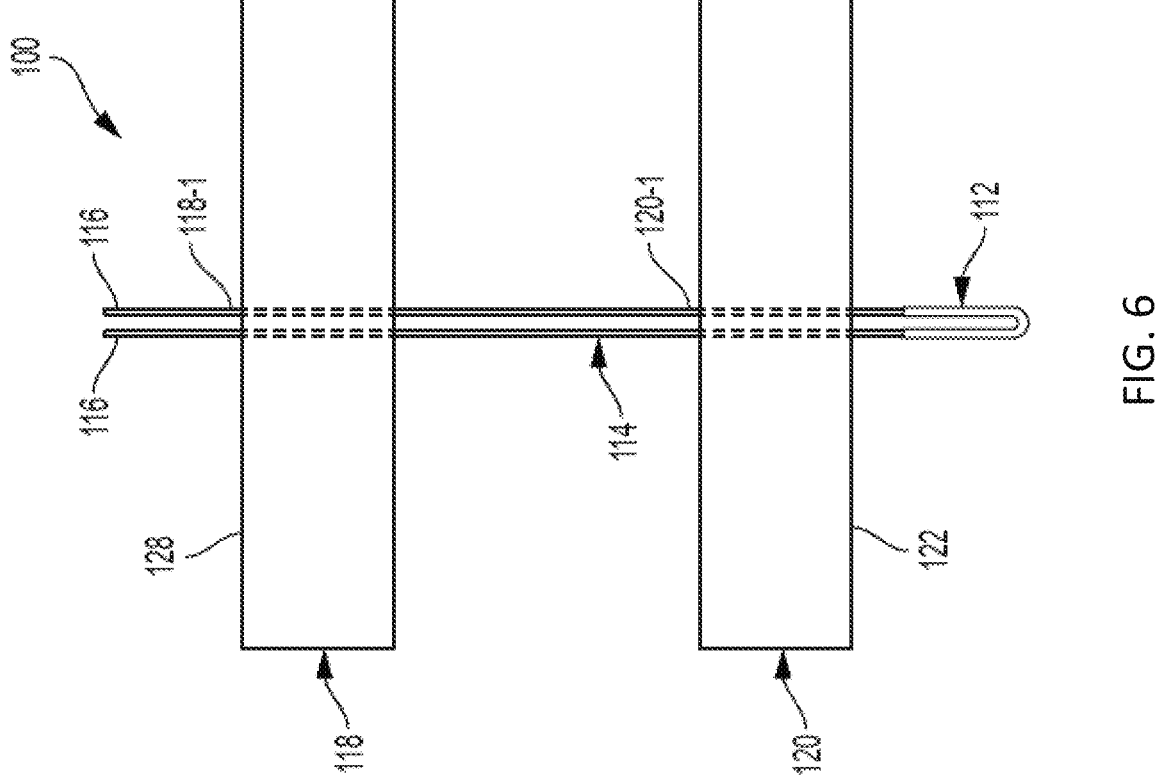
FIG. 6 is a side view schematic representation of a suspension system in a partially deployed configuration, according to an embodiment.
Figure 7:
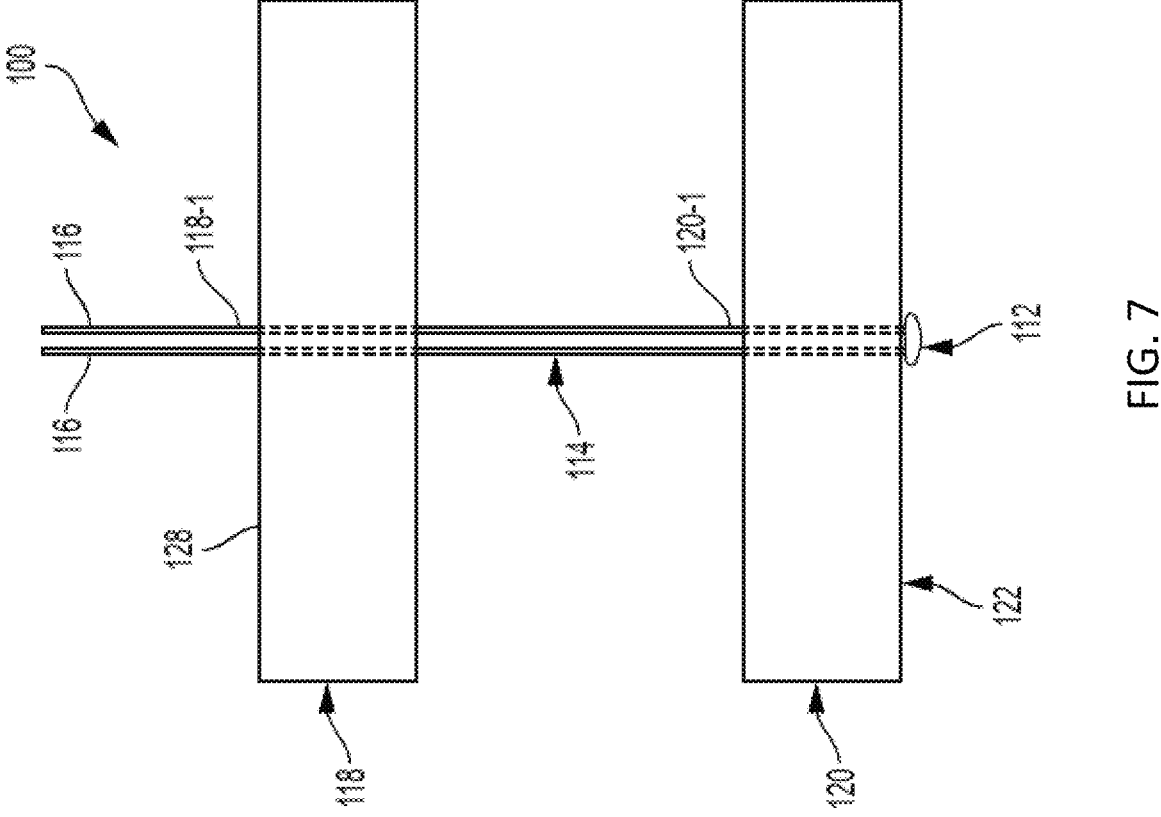
FIG. 7 is another side view schematic representation of the suspension system in a partially deployed configuration, according to an embodiment.

Turning briefly to FIGS. 6-7, there are shown side views schematic representations of a suspension system 100 in a partially deployed configuration, according to an embodiment. As shown, the suture suspension system 100 includes a length of suture 114 woven through an anchoring body 112, as described in U.S. patent application Ser. No. 15/711, 192, assigned to the assignee hereof and incorporated by reference herein in its entirety. In the depicted embodiment, the anchoring body 112 is an all-suture button in an expanded position (FIG. 6) and in a compressed position (FIG. 5). In another embodiment, the anchoring body 112 can be a suspensory fixation device as described in U.S. Pat. No. 9,700,403 assigned to the assignee hereof and incorporated by reference herein in its entirety. In brief, an embodiment of the suspensory fixation device can include an elongated anchor member (which may or may not have preformed suture receiving apertures, where at least one of which can, but doesn't have to be, recessed within a surface of the elongated anchor member), and a suture threaded through at least one of the apertures. In an alternative embodiment, the anchoring body 112 can be any soft suture anchor material (as should be understood by a person of ordinary skill in the art in conjunction with a review of this disclosure). In brief, since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) along with a suture or filament portion. The fibrous construct can be flat, non-flat, and/or tubular or non-tubular. Another example of a "soft" all-suture anchor is the Y-Knot® device. See, e.g., U.S. Pat. No. 9,826,971. Such all-suture anchors can take advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. In the aforementioned embodiments, the suture 114 is woven through the anchoring body 112 such that two free limbs 116 of suture 114 extend from the anchoring body 112. In another embodiment, the anchoring body 112 can be a suspensory fixation device as described in U.S. Pat. Nos. 9,700,403 and 9,931,197, assigned to the assignee hereof and incorporated by reference herein in its entirety. In an alternative embodiment, the anchoring body 112 can be any soft suture anchor material. The suture 114 is woven through the anchoring body 112 such that two free limbs 116 of suture 114 extend from the anchoring body 112.

To utilize the suspension system 100, a single hole 118-1 is formed through a first body 118, and a single hole 120-1 is formed through an adjacent second body 120. The first and second bodies 118, 120 may be soft tissue, bone, or a graft. In the embodiments shown, each of the first body 118 and the second body 120 is bone. As shown in FIGS. 6-7, a length of suture 114 is positioned through the bone hole 118-1, through the bone hole 120-1, through an all-suture button 112, and advanced back through bone holes 120-1 and 118-1 to form the partially deployed configuration shown in FIGS. 6-7—where the length of suture 114 is shown with two free limbs 116 extending proximally from the opposite/proximal/top surface 128 of bone 118, the all-suture button 112 extends distally from the distal surface 122 of second bone 120, and a section of suture 114 forms a bridge between the first bone 118 and the second bone 120.

As depicted in FIG. 7, the free limbs 116 of the suture 114 are pulled proximally from the first bone 118 to set the all-suture button 112 against the distal surface 122 of the second bone 120. As the suture 114 is pulled proximally, the all-suture button 112 moves from the expanded position (in FIG. 6) to a compressed position (in FIG. 7). In the compressed position, the all-suture button 112 covers a surface area on the distal side 122 of the second bone 120 larger than the diameter of the bone hole 120-1 in the second bone 120.

Once the all-suture button 112 is in the compressed position, tension in the suture 114 can be used to create a suspension configuration between the first bone 118 and the second bone 120 by deploying a backstop from an expanded position to a compressed position.

Figure 2:
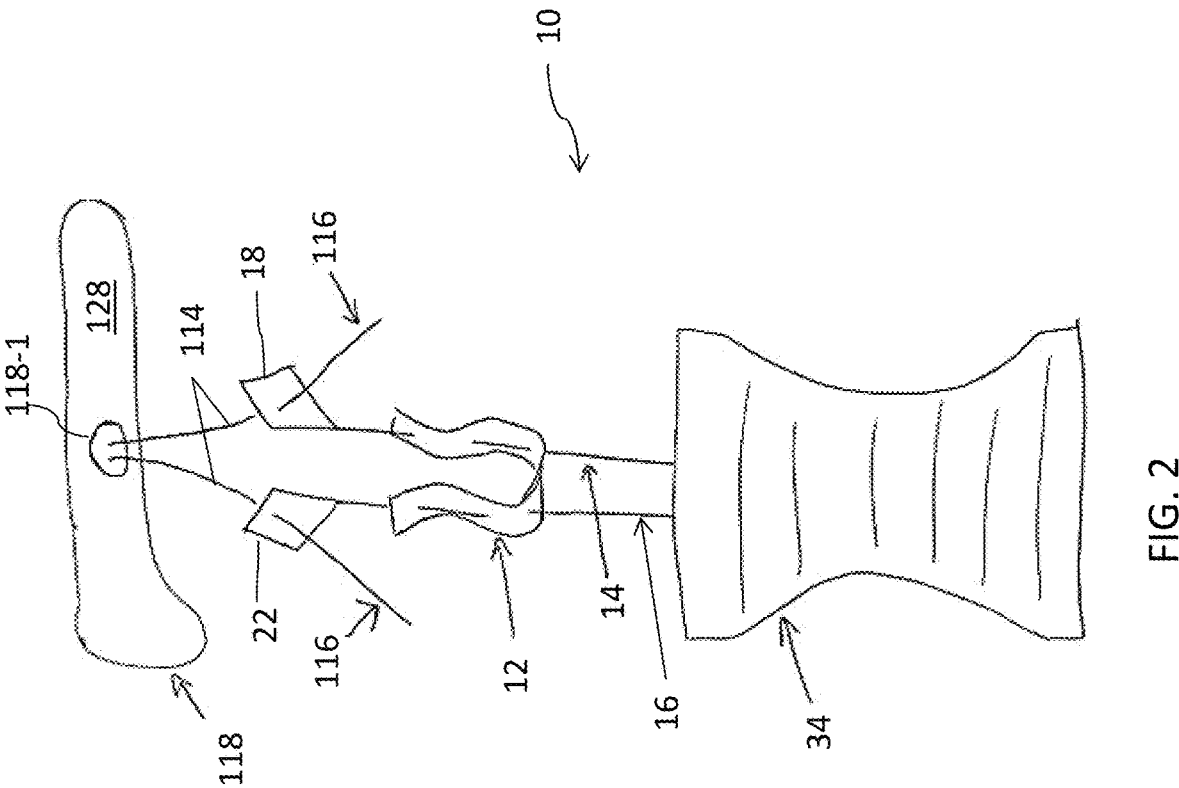
FIG. 2 is a side view schematic representation of the suture backstop system in a partially deployed configuration, according to an embodiment.

Referring now to FIG. 2, there is a side view schematic representation of the suture backstop system 10 in a partially deployed configuration, according to an embodiment. As described above the backstop 12 of the suture backstop system 10 can be used to create suspension between the first bone 118 and the second bone 120 (FIGS. 6-7). During deployment of the suture backstop system 10, the free limbs 116 of suture 114 are pulled through the bone hole 118-1 such that they extend proximally from the proximal surface 128 of the first body 118. The free limbs 116 of suture 114 are then passed through the first and second loops 18, 22 in the suture backstop system 10, as shown in FIG. 2.

Figure 3:
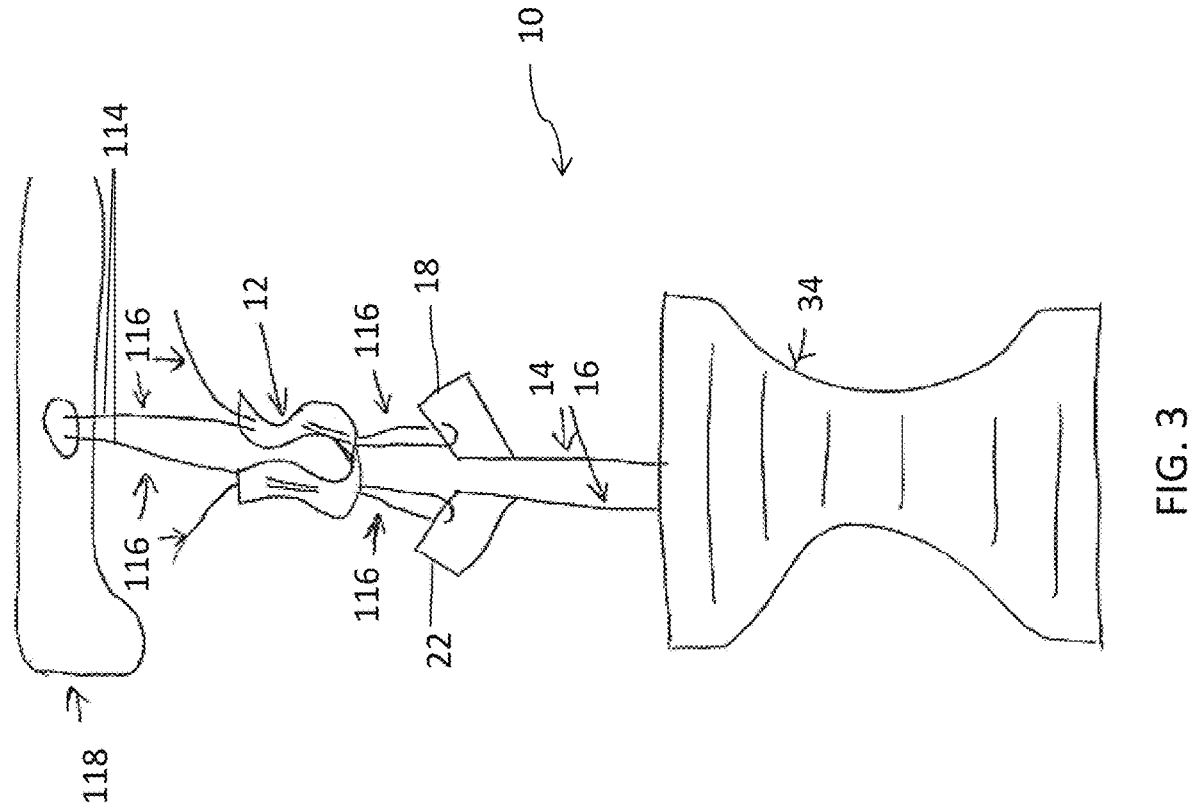
FIG. 3 is another side view schematic representation of the suture backstop system in a partially deployed configuration, according to an embodiment.

Turning now to FIG. 3, there is shown another side view schematic representation of the suture backstop system 10 in a partially deployed configuration, according to an embodiment. After the free limbs 116 of suture 114 are passed through the first and second loops 18, 22, the free limbs 116 of suture 114 are tensioned distally and the handle 34 is simultaneously pulled proximally. By pulling the handle 34 proximally, the first and second loops 18, 22 are pulled through the passing locations 26, 28, 30, 32 on the backstop 12. As the free limbs 116 of suture 114 have been passed through the first and second loops 18, 22, the free limbs 116 are also pulled through the passing locations 26, 28, 30, 32 in the backstop 12 when the first and second loops 18, 22 are pulled through the backstop 12, leading to the partially deployed configuration shown in FIG. 3. Still referring to FIG. 3, the backstop 12 is now loaded on the suture 114 of the suspension system 100 (FIGS. 6-7). Further, the free limbs 116 of suture 114 extend distally toward the proximal surface 128 of the first bone 118 (FIGS. 6-7).

Figure 4:
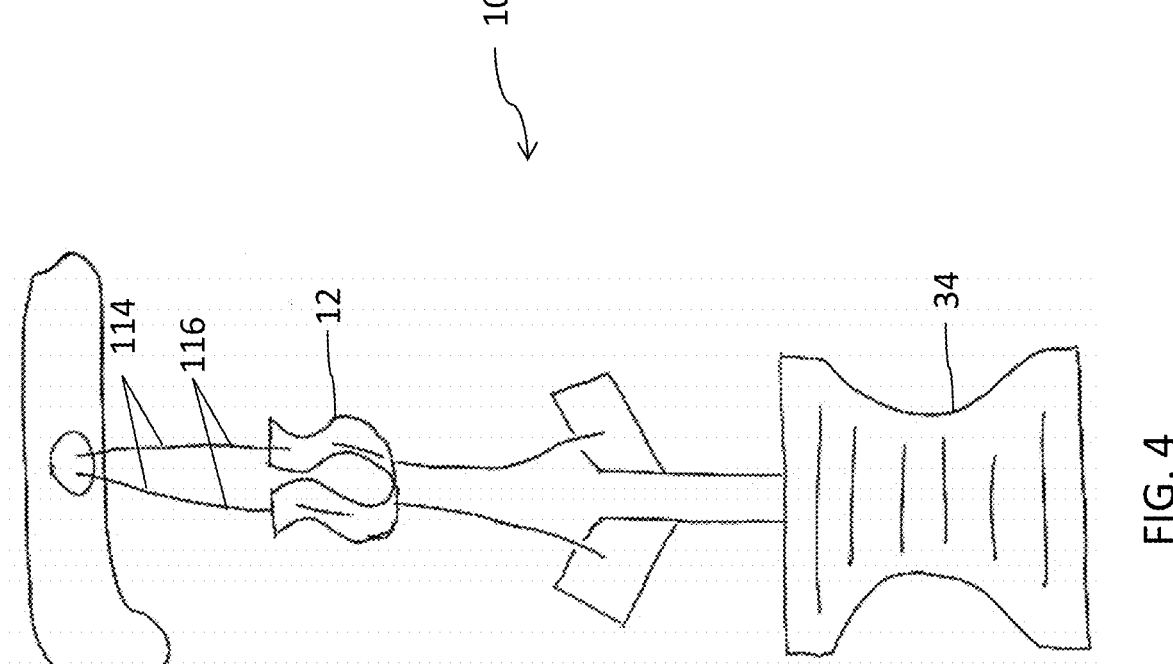
FIG. 4 is an additional side view schematic representation of the suture backstop system in a partially deployed configuration, according to an embodiment.

Referring now to FIG. 4, there is shown an additional side view schematic representation of the suture backstop system 10 in a partially deployed configuration, according to an embodiment. After the backstop 12 is loaded onto the suture 114 of the suspension system 100 (FIGS. 6-7), the handle 34 is again pulled in the proximal direction to slide the free limbs 116 of suture 114 all the way through the backstop 12 to create the partially deployed configuration shown in FIG. 4. Thereafter, the handle 34 be discarded or otherwise removed from the suture backstop system 10.

Figure 8:
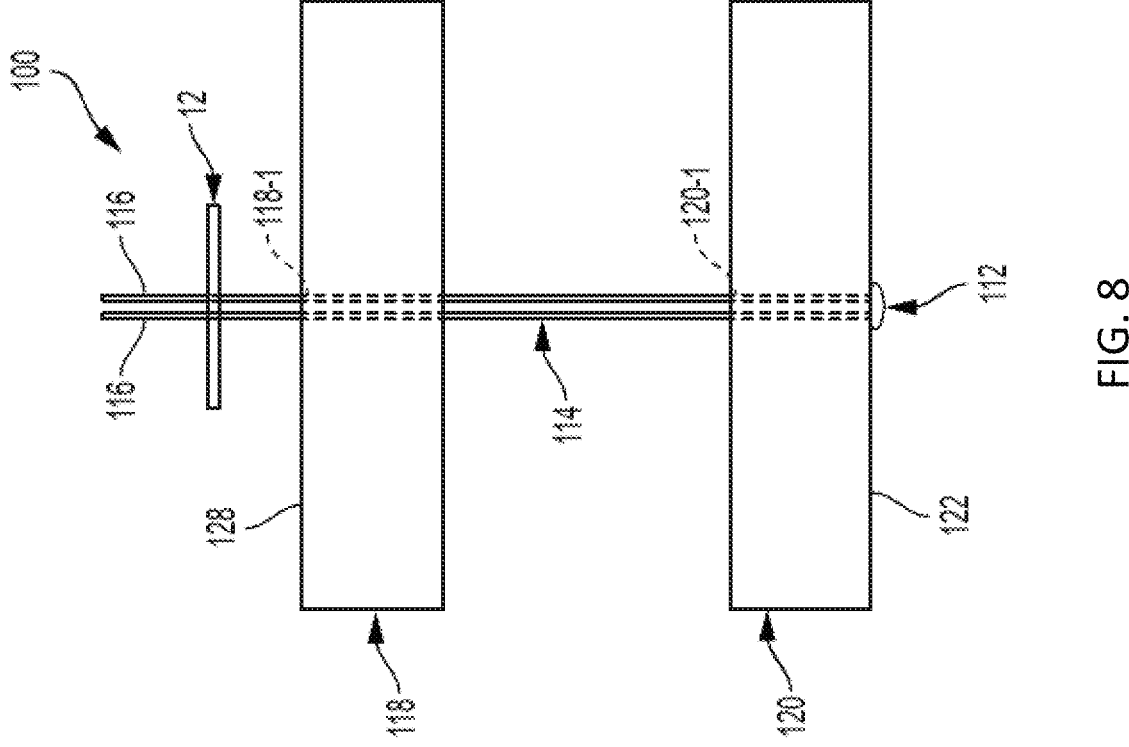
FIG. 8 is a side view schematic representation of the backstop loaded onto the suspension system, according to an embodiment.

Turning now to FIG. 8, the backstop 12 has been transferred to the free limbs 116 of suture 114 and is shown being moved distally along the suture 114 until it is against the proximal surface 128 of the first bone 118. Once the backstop 12 is against the proximal surface 128 of the first bone 118, additional tension in the free limbs 116 in the proximal direction causes the backstop 12 to move from an expanded position to a compressed position. In the expanded position, shown in FIG. 4, the ends 20, 24 of the backstop 12 are in a first direction along a longitudinal axis. When the backstop 12 moves into the compressed position, the ends 20, 24 of the backstop 12 can rotate to a second direction different than the first direction, as shown in FIG. 5 vs. FIG. 4 (but don't have to, they can face the same direction during/after the described movement). Other compressed positions are contemplated in which the backstop 12 covers a surface area on the proximal surface 128 of the first bone 118 greater than the diameter of the bone hole 118-1. Purposes of the backstop 12 structure, configuration, positioning and related functionality include preventing the suture 114 from pulling out from the first bone hole 118-1 and to maintain the tension in the suture 114 between the backstop 12 and the all-suture button 112.

Figure 9:
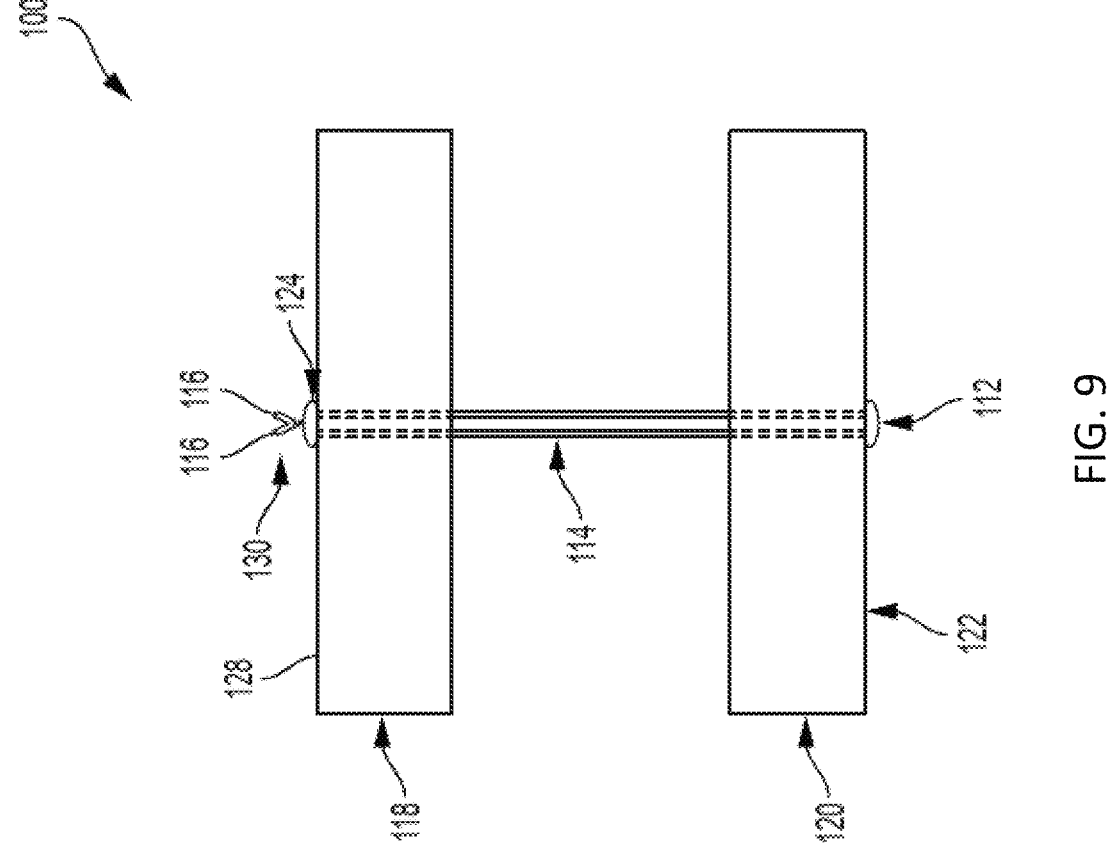
FIG. 9 is a side view schematic representation of the backstop and the suspension system in the deployed configuration, according to an embodiment.

As shown in FIG. 5, the backstop 12 is in the deployed configuration, according to an embodiment. The free limbs 116 of suture 114 are tied over the backstop 12 in the compressed position, forming a knot 130. The knot 130 forces the backstop 12 to lay tight over the proximal surface 128 of the first bone 118 and particularly, the bone hole 118-1 (FIG. 8), to form the button and complete the repair. FIG. 9 shows a side schematic view of the knot 130 formed in the free limbs 116 of suture 114 proximally over the backstop 12, i.e., the deployed configuration of the suspension system 100. Tying the knot 130 in the free limbs 116 secures the backstop 12 in the compressed and deployed position. Excess portions of the free limbs 116 of suture 114 that extend from the knot 130 can be trimmed and removed to decrease the potential for irritation and discomfort.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A suture backstop system, comprising
a backstop having a central longitudinal axis extending between a first end and a second end, wherein the first end comprises a first surface and the second end comprises a second surface opposite the first surface when the backstop is in a first position fully extending along the central longitudinal axis;
a first passing longitudinal element woven through the backstop such that a first loop having a first opening is created in the first passing longitudinal element and extends from the first end of the backstop;
a second passing longitudinal element separate from the first passing longitudinal element and woven through the backstop such that a second loop having a second opening is created in the second passing longitudinal element and extends from the second end of the backstop, and
wherein the backstop is in a second position when the first passing longitudinal element and the second passing longitudinal element are each woven therethrough, wherein when in the second position, each of the first surface of the backstop and the second surface of the backstop face a distal direction.

2. The system of claim 1, wherein the first and second passing longitudinal elements are woven through the backstop at multiple passing locations.

3. The system of claim 1, wherein the first passing longitudinal element is woven through the backstop at three passing locations and the second passing longitudinal element is woven through the backstop at an additional three passing locations.

4. The system of claim 1, wherein the first passing longitudinal element extends proximally from the backstop at a first central passing location and the second passing longitudinal element extends proximally from the backstop at an adjacent, second central passing location.

5. The system of claim 1, further comprising one or more ridges on a handle.

6. The system of claim 1, wherein the backstop is composed of all-suture material.

7. The system of claim 1, wherein each of the first passing longitudinal element and the second passing longitudinal element are formed of nitinol.

8. The system of claim 1, further comprising a handle having a handle central longitudinal axis, a proximal end and a distal end, wherein the distal end is attached to the first passing longitudinal element and the second passing longitudinal element.

9. The system of claim 8, wherein the first loop comprises a first side extending along a first plane being substantially parallel to the handle central longitudinal axis, a second side connected to the first side and extending along a second plane positioned at an angle to the handle central longitudinal axis, a third side opposite the first side and connected to the second side, and a fourth side opposite the second side and connected to the first side and to the third side, wherein each of the first side, the second side, the third side and the fourth side face the first opening.

* * * * *